United States Patent [19]

Zahorian et al.

[11] Patent Number: 5,524,631
[45] Date of Patent: Jun. 11, 1996

[54] PASSIVE FETAL HEART RATE MONITORING APPARATUS AND METHOD WITH ENHANCED FETAL HEART BEAT DISCRIMINATION

[75] Inventors: Stephen A. Zahorian, Norfolk; David L. Livingston, Salem, both of Va.; Robert A. Pretlow, III, Redmond, Wash.

[73] Assignee: The United States of America as represented by the Administrator of the National Aeronautics and Space Administration, Washington, D.C.

[21] Appl. No.: 323,943

[22] Filed: Oct. 13, 1994

[51] Int. Cl.⁶ ................................ D61B 5/0444
[52] U.S. Cl. .................................... 128/698
[58] Field of Search .............................. 128/698

[56] References Cited

U.S. PATENT DOCUMENTS

| | | |
|---|---|---|
| 4,456,959 | 6/1984 | Hirano et al. ............ 128/698 |
| 4,781,200 | 11/1988 | Baker . |
| 4,965,725 | 10/1990 | Rutenberg . |
| 5,092,343 | 3/1992 | Spitzer et al. . |
| 5,140,992 | 8/1992 | Zuckerwar et al. . |
| 5,209,237 | 5/1993 | Rosenthal . |
| 5,257,627 | 11/1993 | Rapoport . |
| 5,280,792 | 1/1994 | Leong et al. . |
| 5,331,550 | 7/1994 | Stafford et al. . |

OTHER PUBLICATIONS

IJCNN International Joint Conference on Neural Networks, Baltimore, MD, Jun. 7–11, 1992, "Artificial Neural Network for ECG Arrhythmia Monitoring" by Hu et al., pp. II–987 to II–992.

Signal Processing Methodologies For An Acoustic Fetal Heart Rate Monitor, by R. A. Pretlow, III, Old Dominion University, Apr., 1991.

*Primary Examiner*—William E. Kamm
*Attorney, Agent, or Firm*—Kimberly A. Chasteen

[57] ABSTRACT

An apparatus for acquiring signals emitted by a fetus, identifying fetal heart beats and determining a fetal heart rate. Multiple sensor signals are outputted by a passive fetal heart rate monitoring sensor. Multiple parallel nonlinear filters filter these multiple sensor signals to identify fetal heart beats in the signal data. A processor determines a fetal heart rate based on these identified fetal heart beats. The processor includes the use of a figure of merit weighting of heart rate estimates based on the identified heart beats from each filter for each signal. The fetal heart rate thus determined is outputted to a display, storage, or communications channel. A method for enhanced fetal heart beat discrimination includes acquiring signals from a fetus, identifying fetal heart beats from the signals by multiple parallel nonlinear filtering, and determining a fetal heart rate based on the identified fetal heart beats. A figure of merit operation in this method provides for weighting a plurality of fetal heart rate estimates based on the identified fetal heart beats and selecting the highest ranking fetal heart rate estimate.

32 Claims, 7 Drawing Sheets

PASSIVE FETAL HEART RATE MONITORING APPARATUS AND METHOD WITH ENHANCED FETAL HEART BEAT DISCRIMINATION

ORIGIN OF THE INVENTION

The invention described herein was jointly made in the performance of work under a NASA contract and under a NASA Grant, and is subject to Section 305 of the National Aeronautics and Space Act of 1958, as amended, Public Law 85-568 (72 Stat. 435; 42 USC 2457) and Public Law 96-517 (35 U.S.C. 200 et seq.). In accordance with 35 USC 202, the grantee elected not to retain title.

BACKGROUND OF THE INVENTION

1. Field of the Invention

The invention relates in general to the determination of the fetal heart rate of a fetus inside an expectant mother through the identification of fetal heart beats, and more specifically, to an improved method and apparatus for detecting fetal heart beats from the signals generated by a passive fetal heart rate monitoring sensor and determining a fetal heart rate based on the identified fetal heart beats.

2. Description of the Related Art

Various methodologies have been employed in the industry to determine fetal heart rates within a noise-contaminated signal from a fetal heart monitoring sensor. For example, a well known method in the industry is bandpass filtering which removes low frequency noise from heart beat signals. However, bandpass filtering fails to adjust for background noise frequencies which change with respect to time. A more sophisticated methodology which adapts to changing background noise is described in U.S. Pat. No. 4,781,200 to Baker. The Baker patent discloses a portable, non-invasive system for monitoring fetal heart rate employing adaptive cancellation and spectral analysis. The Baker system is essentially an ambulatory system which uses adaptive interference cancelling to isolate fetal heart beats and frequency domain analyses of multi-channel signals to extract useful information pertaining to fetal well-being, including fetal heart rate and absence of fetal movement. Another system, described in U.S. Pat. No. 5,209,237 to Rosenthal, also employs a similar noise cancellation technique, but uses multiple reference sensors to detect various background noises for adaptive cancellation and subsequent time-domain, cross-spectral frequency analysis. While there are certain benefits in using adaptive cancellation and spectral analysis, the use of interference cancellation to identify fetal heart beats is dependent on the quality of the reference signals. Noise not included in the reference signal may not be filtered from the signals emanating from the abdomen. While generally known sources of noise, such as the mother's heart beat and breathing, are easily identified and filtered, extraneous noise from other organs or from the external environment may be missed. Therefore, the resulting signal may not have been sufficiently filtered of noise and an inaccurate fetal heart rate may have been determined from erroneous fetal heart beat data.

The use of a linear prediction methodology has also been used in the industry as the basis for identifying fetal heart beats during the determination of a fetal heart rate. Such an approach is described in Pretlow III, R. A. and Stoughton, J., "Signal Processing Methodologies for an Acoustic Fetal Heart Rate Monitor," Master's Thesis, April, 1991, Old Dominion University (hereafter "Pretlow et al."). However, such a methodology, while an improvement over adaptive cancellation, is still sensitive to noise not related to the fetal heart beat. Moreover, linear prediction has a significant deficiency inherent in the linear nature of its filter structure which prevents it from accurately modeling the nonlinearity of the background noise. The use of a two-layer, feed forward neural network has been suggested for use in identifying heart beats and determining heart rates. Such a method is discussed in detail in Hu, Y. H., Tompkins, W. J., and Xue, Q., "Artificial Neural Network for ECG Arrhythmia Monitoring," Proceedings of IJCNN Intl. Joint Conf. on Neural Networks, 1992, vol. 2 (hereafter "Hu et al."). However, the drawback of the methodology discussed by Hu et al. is that it concentrates on eliminating noise from ECG data and does not deal with supporting an acoustic-based monitoring apparatus. Indeed, the ECG environment differs significantly from the acoustic signal environment for fetal heart beats in terms of the type and amount of noise and the strength of the heart beat signal. The previously-mentioned Pretlow et al. article acknowledges the possibility of using a neural network to perform signature matching to identify a fetal heart beat, but concludes that neural network processing works best in offline waveform processing, such as for ECG analysis, and has not been found practical for real time fetal heart beat detection.

SUMMARY OF THE INVENTION

Accordingly, it is an object of the invention to overcome the previously described problems and deficiencies in existing technology for identifying fetal heart beats and determining an accurate fetal heart rate.

In addition, it is an object of the invention to provide an improved apparatus and method for identifying fetal heart beats and determining fetal heart rates from signals generated from an acoustic fetal heart monitoring sensor.

It is a further object of the invention to provide a more accurate apparatus and method for identifying a fetal heart beat, through the simultaneous nonlinear filtering of a plurality of acoustic signals, generated by a passive fetal heart rate monitoring sensor, by the use of a Teager Energy Operator and/or a neural network nonlinear filter or filters, and determining a fetal heart rate based upon the identified fetal heart beats.

In order to achieve the foregoing and other objects, in accordance with the purposes of the present invention as described therein, an apparatus for identifying fetal heart beats and determining a fetal heart rate comprises a passive fetal heart monitoring sensor producing a plurality of acoustic signals, multiple nonlinear filters simultaneously filtering the plurality of sensor signals, and means for determining fetal heart rates. As embodied herein, there is a passive fetal heart rate monitoring sensor which acquires acoustic signals emitted from a fetus inside a body and outputs a plurality of sensor signals; a signal processing device, which receives, amplifies, filters, multiplexes, and digitizes the plurality of sensor signals, and which outputs a plurality of processed signals; multiple parallel nonlinear filters, which receive the plurality of processed signals, filter each of the plurality of processed signals to identify fetal heart beats, and output a plurality of functional values indicative of the presence of fetal heart beats for each of the plurality of processed signals; and fetal heart rate determining means, responsive to the plurality of functional values indicative of the presence of fetal heart beats, for determining and outputting a fetal heart rate.

A method for identifying fetal heart beats and determining fetal heart rates comprises multiple parallel nonlinear filtering of a plurality of acoustic sensor signals generated from a passive fetal heart rate monitoring sensor and steps for determining a fetal heart rate based on the identified heart beats. As embodied herein, the method comprises a step for acquiring acoustic signals emitted from the fetus and outputting a plurality of sensor signals, a step for receiving, amplifying, filtering, multiplexing, and digitizing the plurality of sensor signals to produce a plurality of processed signals, a step for multiple parallel nonlinear filtering of each of the plurality of processed signals to identify the presence of fetal heart beats and to output a plurality of functional values indicative of the presence of fetal heart beats for each of the plurality of processed signals, and a step for determining and outputting the fetal heart rate based on the plurality of functional values indicative of the presence of fetal heart beats.

BRIEF DESCRIPTION OF THE DRAWINGS

The present invention and the objects achieved by it will be understood from the description of the preferred embodiments, taken in conjunction with the accompanying drawings of which.

DETAILED DESCRIPTION OF THE PREFERRED EMBODIMENTS

Reference will now be made in detail to the present preferred embodiments of the present invention, examples of which are illustrated in the accompanying drawings, wherein like reference numerals refer to like elements throughout.

Figure 1:
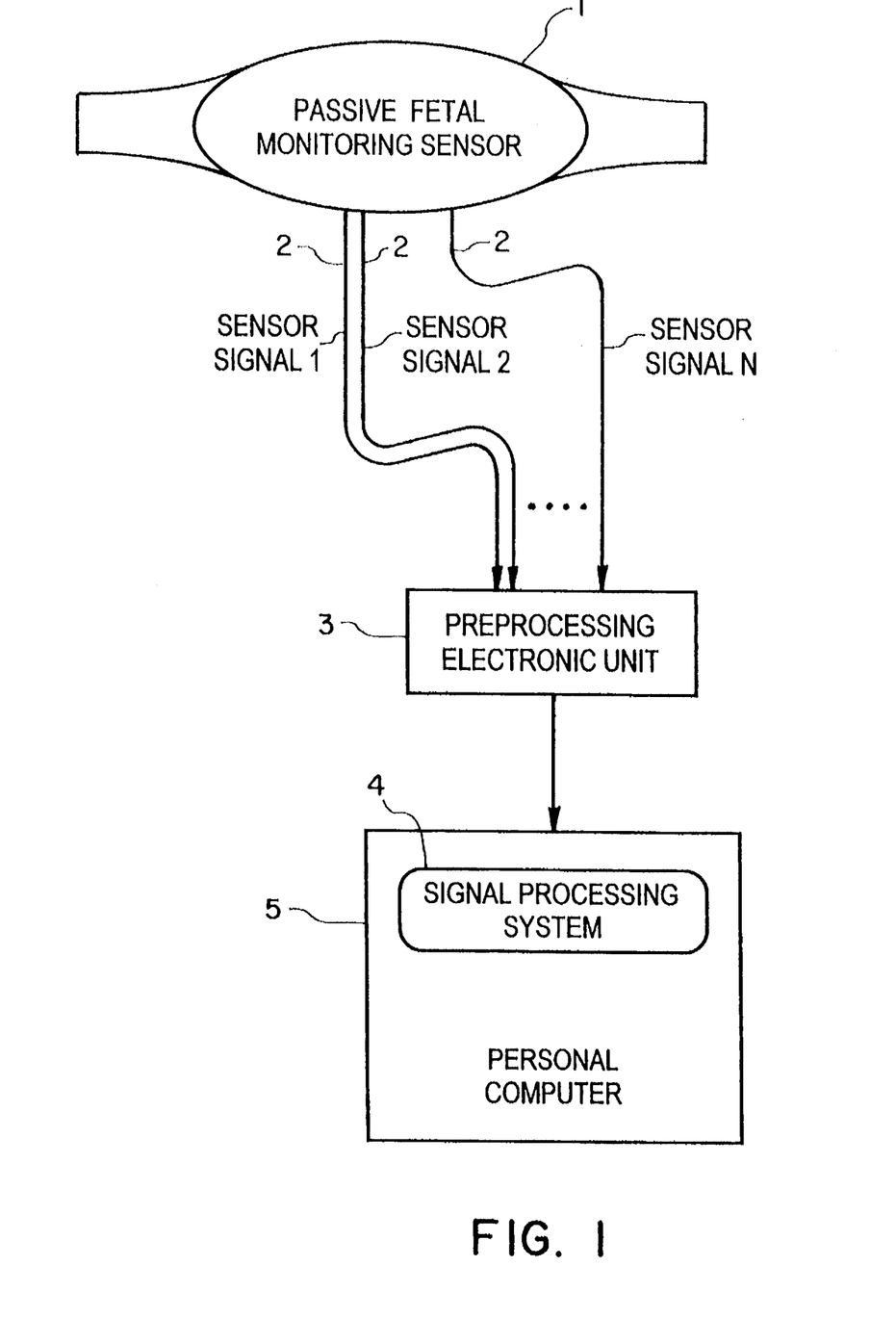
FIG. 1 is an overview of the hardware platform for an embodiment of an apparatus according to the present invention.

FIG. 1 is an overview of the hardware platform for an apparatus according to an embodiment of the present invention. In FIG. 1, an ambulatory, non-invasive, passive, fetal heart rate monitoring sensor 1 is placed on the abdomen of an expectant mother. Multiple sensor elements inside sensor 1 receive the signals emitted by a fetus inside the expectant mother and output a plurality of corresponding sensor signals 2, commensurate with the number of sensor elements inside sensor 1. Such ambulatory, non-invasive, sensor elements are well known in the industry and an example of this type of sensor 1 is described in U.S. Pat. No. 5,140,992 to Zucherwar et al. entitled "PASSIVE FETAL MONITORING SENSOR." The plurality of sensor signals 2 are received by a preprocessing electronic unit 3 which amplifies, filters, and multiplexes the signals in order to prepare and organize the sensor signals 2 for further processing. The preprocessed signals outputted by the preprocessing electronic unit 3 are received by the signal processing system 4 which demultiplexes the preprocessed signals back into multiple sensor signals and digitizes the preprocessed multiple sensor signals for further analysis by an improved method of identifying fetal heart beats and determining a fetal heart rate. In particular, multiple parallel nonlinear filters are used in achieving significantly more accurate results for the identification of fetal heart beats. Moreover, the determination of multiple fetal heart rate estimates, one estimate from the result of each nonlinear filtering of each sensor signal, and the use of a figure of merit method to select the best fetal heart rate estimate ensures the most accurate result from this system. The signal processing system 4 is programmed to carry out these functions of heart beat identification and heart rate determination.

Figure 2:
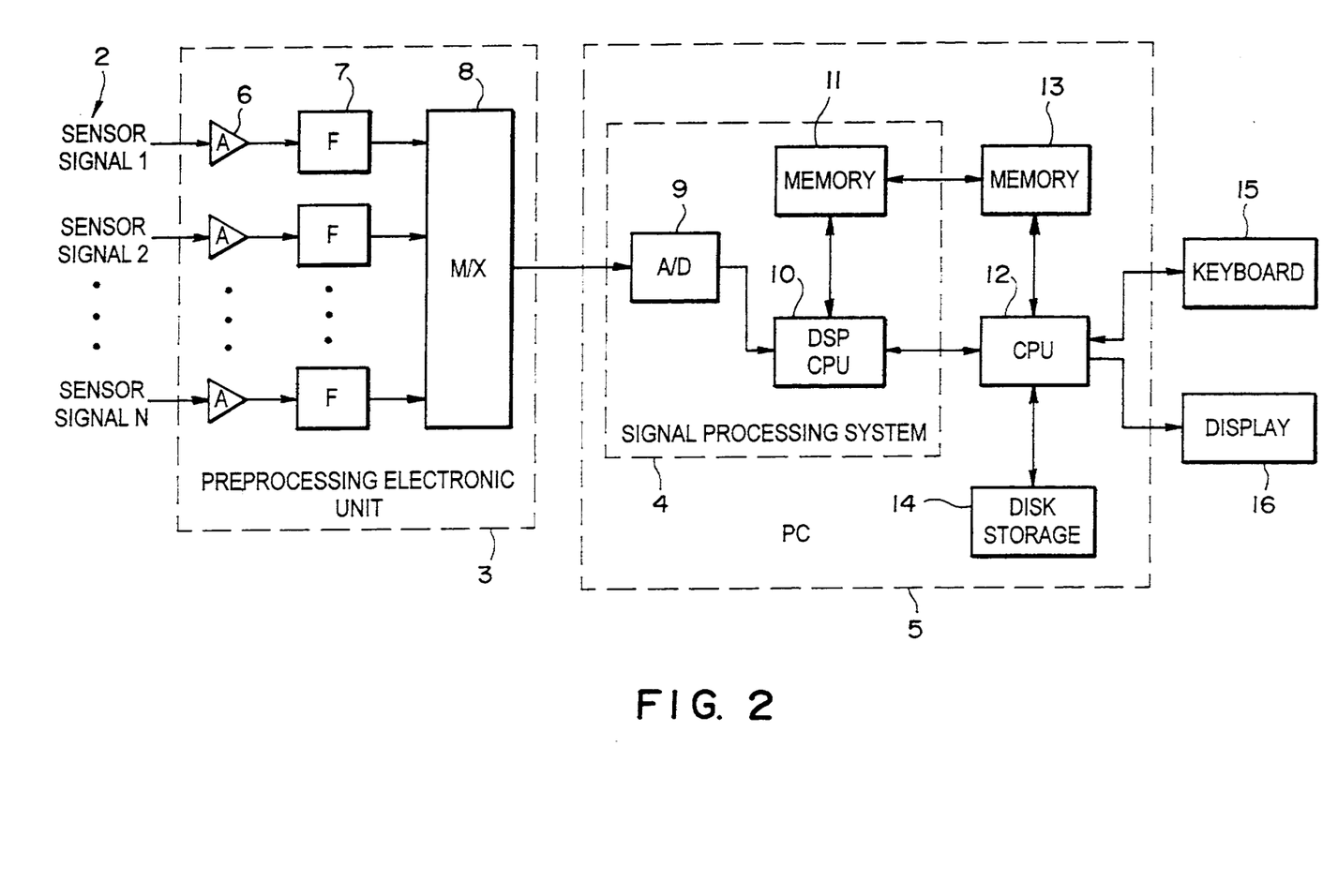
FIG. 2 is a block diagram of the pre-processing hardware, the signal processing system, and the computer for an embodiment of an apparatus according to the present invention.

As to the signal processing system 4, one embodiment of the present invention has the signal processing system 4 inside a personal computer (PC) 5. The PC 5 is well known in the industry and, as shown in FIG. 2, is comprised of a central processing unit (CPU) 12, memory 13, and fixed disk storage 14; and further, has attached a keyboard 15 and a display 16. The PC 5 is used to carry out input from and output to various devices, such as the keyboard 15, the display 16, or a communications channel (not shown). The signal processing system 4 is not limited to being physically located inside a PC. For example, the preprocessing electronic unit 3 and the signal processing system 4 can be combined in a signal processing device separate from the PC. In addition, the embodiments of the present invention are not limited to the identification of fetal heart beats and determination of fetal heart rates by a programmed signal processing system 4. For example, a general purpose digital computer, such as a generic version of PC 5, may be programmed to provide the same features. After a fetal heart rate is determined, the result may be displayed on display 16 or stored in fixed storage 14 in the PC, for example, when appropriate commands are entered via the keyboard 15.

FIG. 2 is a block diagram detailing the preprocessing electronic unit 3, the signal processing system 4, and the PC 5. The preprocessing electronic unit 3 comprises amplifiers 6 which receive the plurality of sensor signals 2. The sensor signals 2 outputted by the passive fetal heart rate monitoring sensor 1 is weak due to the inherent weakness of a fetal heart beat. One purpose of the amplifiers 6 is to boost the initial sensor signals 2. Another purpose of the amplifiers 6 is to amplify the sensor signals 2 to match the range of subsequent components, e.g. an analog-to-digital converter. The amplifiers 6 respectively are connected to corresponding filters 7. The sensor signals 2 are bandpass filtered by bandpass filters 7 in order to eliminate competing signals that are larger than the fetal heart beat signal. By focusing the bandwidth on the relevant range of a fetal heart beat, the analog-to-digital converter and other subsequent processing will not be saturated with non-essential signals. The bandpass filters 7 are connected to an analog time-division multiplexor (M/X) 8. The multiplexor rotates among the filtered signals and time-division multiplexes the filtered signals to allow simultaneous sampling of all sensor signals. The time slice for each signal is very small (e.g., 0.5 ms) to accommodate the monitoring of dynamic, real-time changes in fetal heart rates. The multiplexor 8 is connected to an analog-to-digital converter 9 in the signal processing system 4. In one embodiment, the signal processing system is a digital signal processing (DSP) card housed inside PC 5. The signal processing system 4 has a central processing unit (CPU) 10 and memory 11 in addition to signal processing electronics (e.g., analog-to-digital converter 9). However, the embodiments of the present invention are not limited to having a signal processing system 4 as a DSP card residing inside a PC. For example, the preprocessing electronic unit 3 may be combined with the features and functions of the signal processing system 4 in a separate signal processing device outside the PC. As a further example, a general purpose digital computer, such as a generic version of PC 5, may be programmed to provide the same features as the signal processing system 4. The preprocessed signal outputted from the preprocessing electronics unit 3 is received by the signal processing system 4. The signal processing system 4 first converts the analog preprocessed signal into digital words, at a specified sampling rate, e.g., 500 Hz or waveform samples per second. Processing performed by the DSP CPU 10 receives the digital words via data stored in the DSP memory 11 and demultiplexes the digitized signal so that further processing may address time slices of digitized acoustic data for each of the multiple sensor signals 17 (as shown in FIG. 3).

Figure 3:
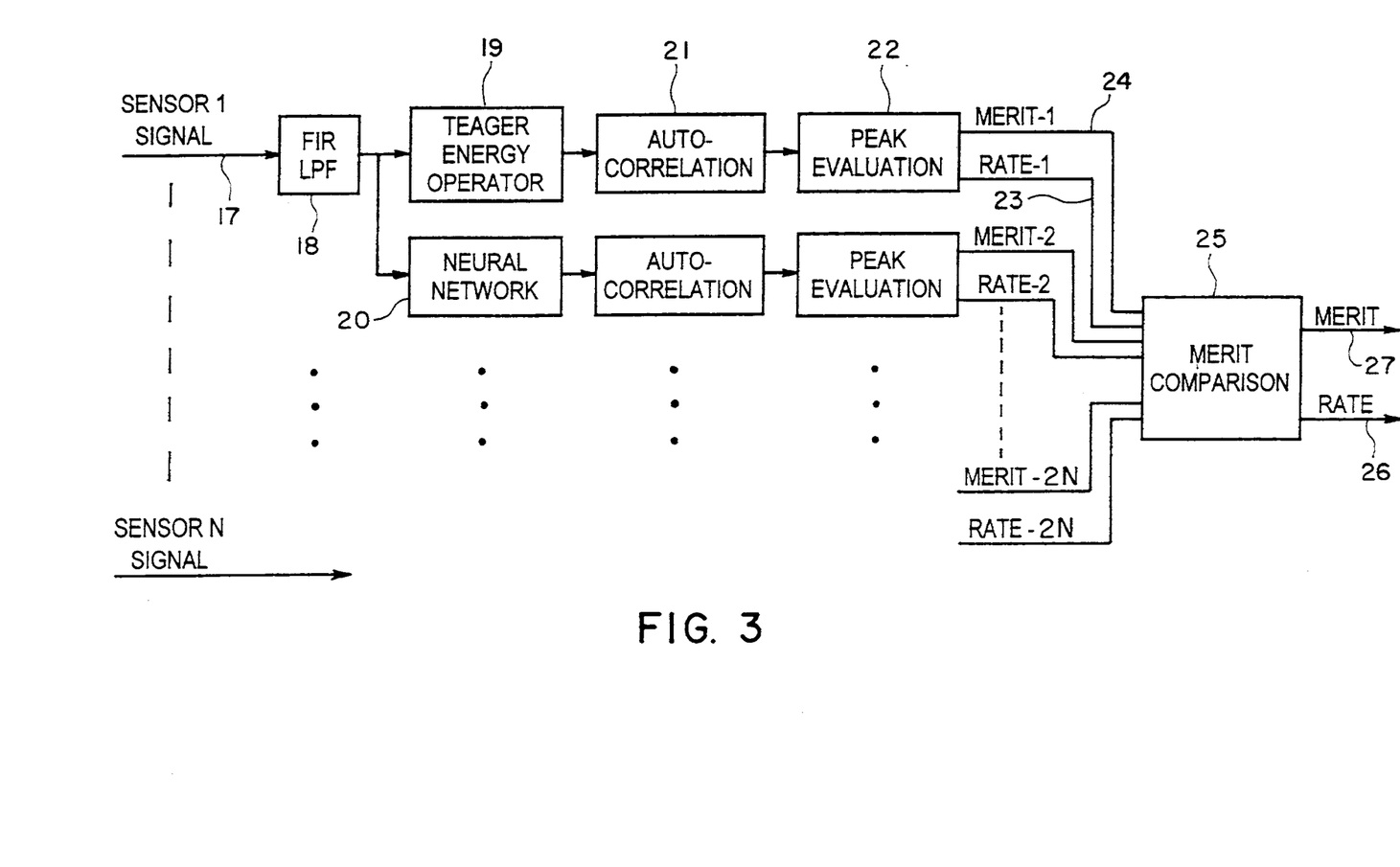
FIG. 3 is a flow chart illustrating the multiple parallel nonlinear filtering for the multiple sensor signals and the determination of a fetal heart rate for an embodiment of a method according to the present invention.

FIG. 3 is a flow chart showing further processing by the DSP CPU 10 of the signal processing system 4. The digitized signal is further filtered (e.g., at a 500 samples per second rate) with a linear phase FIR digital filter 18 ("FIR LPF"). The use of digital filters operating on the digitized signal reduces the requirements on the analog bandpass filters 7 used in the hardware of the preprocessing electronics unit 3 and allows for greater flexibility since these filters are very easily changed or tailored to any reasonable desired response. The linear phase property of the FIR digital filter also insures minimal waveform distortion. The filtered digital signal may then be further decimated to a lower sampling rate (e.g., 250 samples per second). Such decimation to a lower sampling rate may be desirable since it reduces the computations required in subsequent steps of processing.

After the digital filtering of the multiple sensor signal data 17 by filters 18, the signals are further analyzed to identify fetal heart beats and a resultant fetal heart rate is determined from the identified fetal heart beats. Multiple parallel nonlinear filters are used to identify fetal heart beats from the digitized acoustic sensor data. FIG. 3 shows two such nonlinear filters, i.e. a Teager Energy Operator 19 and a neural network 20. These nonlinear filters operate in parallel and provide redundant identification of fetal heart beats for each of the plurality of sensor signals 17. Such parallel redundant processing improves the accuracy of identifying the fetal heart beats. While these benefits are created by the use of multiple parallel nonlinear filters, the embodiments of the invention are not limited to multiple parallel nonlinear filters. For example, singular nonlinear filtering, by the Teager Energy Operator 19 or by the neural network 20, of the plurality of sensor signals 17 is also possible to yield improved identification of fetal heart beats.

Figure 4:
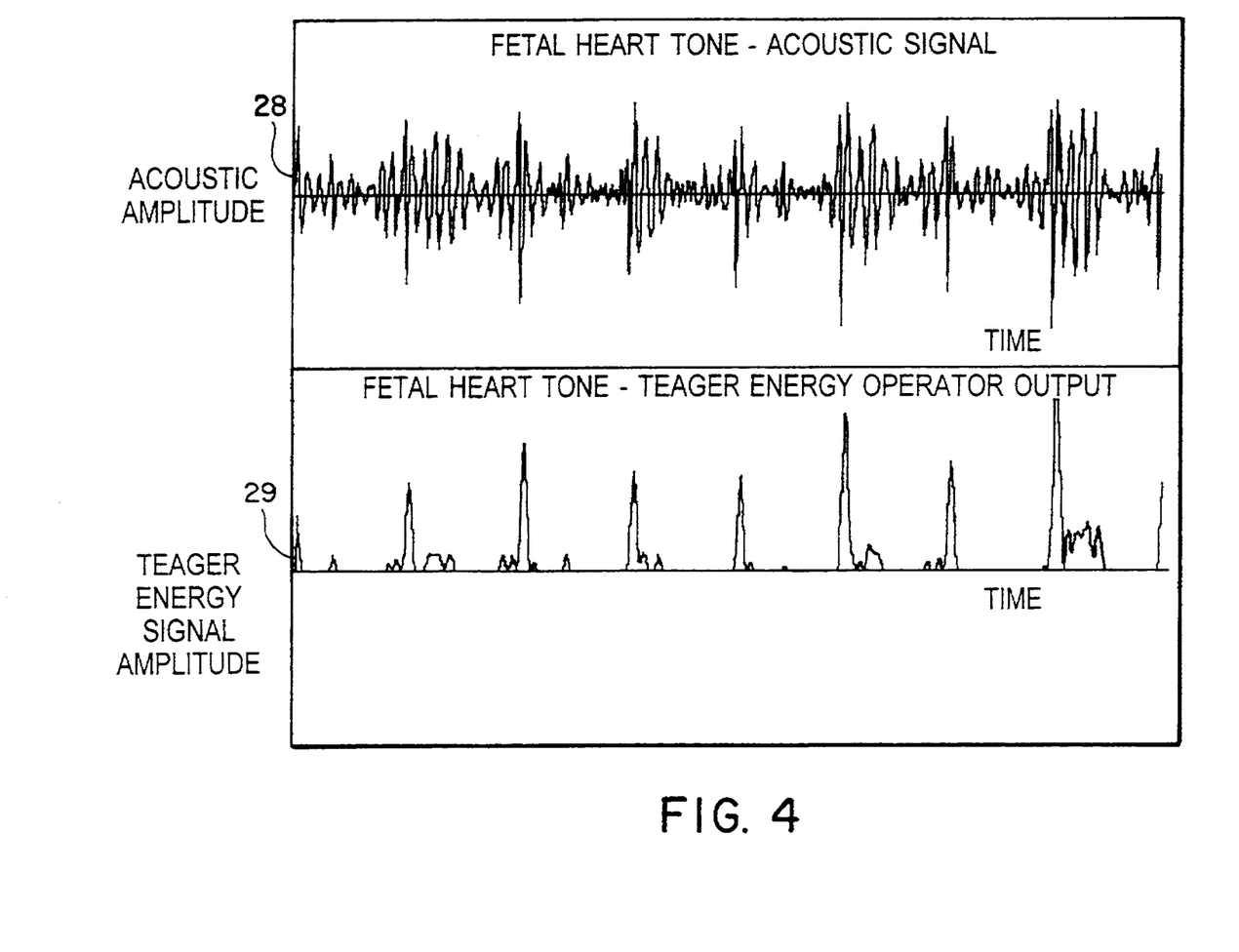
FIG. 4 is a graph depicting the time domain acoustic fetal heart signal and the Teager Energy Operator response to the acoustic signal according to an embodiment of the present invention.

The particular embodiment in FIG. 3 shows a first nonlinear filtering by a Teager Energy Operator 19. The Teager Energy Operator 19 highlights regions of high energy (i.e., the heart beats). This nonlinear filter is known in the industry and is described in Kaiser, James F., "On a Simple Algorithm to Calculate the 'Energy' of a Signal," ICASSP-90, 1990, vol. 1, pp. 381–84 (hereafter "Kaiser"). The Teager Energy Operator is computed using $$y(n) = x^2(n-1) - x(n)*x(n-2),$$

where $x(n)$ is the acoustic signal and $y(n)$ is the Teager energy signal. This nonlinear operation results in a large output in regions which contain high amplitude and rapidly varying signals. The Teager signal is further digitally smoothed using a "box-car" average filter, well known in the industry. FIG. 4 depicts an example of an acoustic signal 28 and the Teager Energy Operator filtered response signal 29. The acoustic signal 28 shown in FIG. 4 is the amplitude of the acoustic signal as time passes. The Teager Energy Operator filtered response signal 29 is the amplitude of the Teager Energy signal as time passes.

Figure 5:
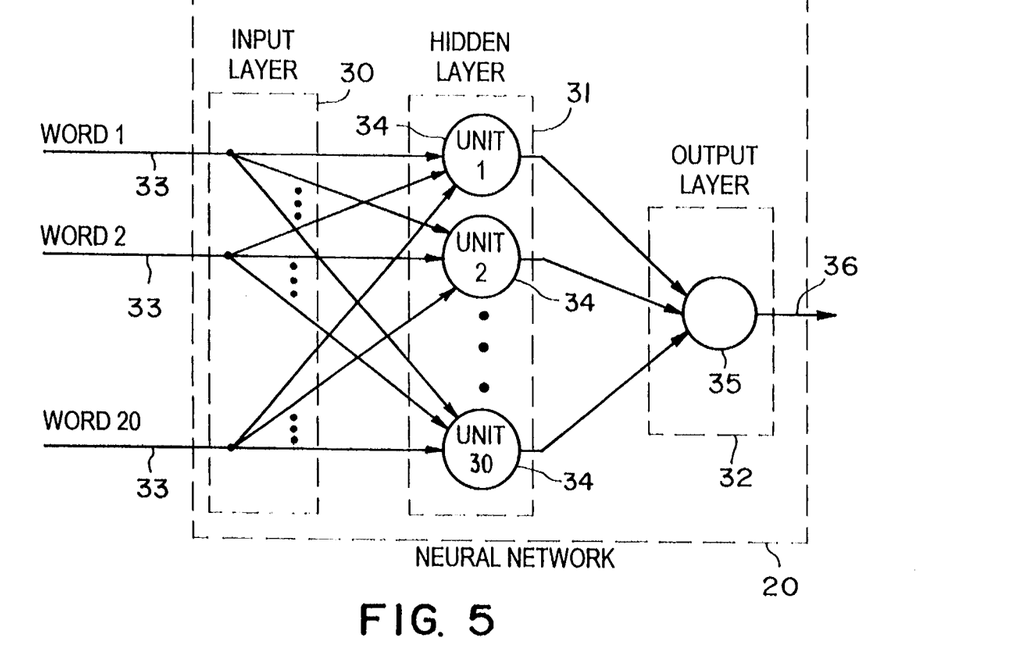
FIG. 5 is a schematic view illustrating a neural network according to an embodiment of the present invention.

The other nonlinear filter shown in FIG. 3 is a neural network. In one embodiment of the present invention, the neural network 20 is a three-layer feed-forward neural network as shown schematically in FIG. 5. The three layers of the network include an input layer 30, a hidden layer 31, and an output layer 32. For this nonlinear filter, the data is first normalized by a root mean square (RMS) value to insure that the subsequent processing receives data of uniform amplitude. In other words, the RMS value of each sampled signal may be used to control or adjust the input range of the analog-to-digital converter to match the measured signal level. Such a normalization method helps to maintain the best possible signal-to-noise ratio for the signal data. The data is then processed by the neural network 20 which nonlinearly "filters" the data using twenty digital words 33 (corresponding to the current input point plus nineteen previous input points 36) to compute an output point 36 for the current time frame, using an equation:

$$y(n) = f\{x(n), x(n-1), \ldots x(n-19)\},$$

for each index in the frame of data, where y(n) is the current neural network output data 36 f represents the neural network x(n) is the current input data point 36

Figure 6:
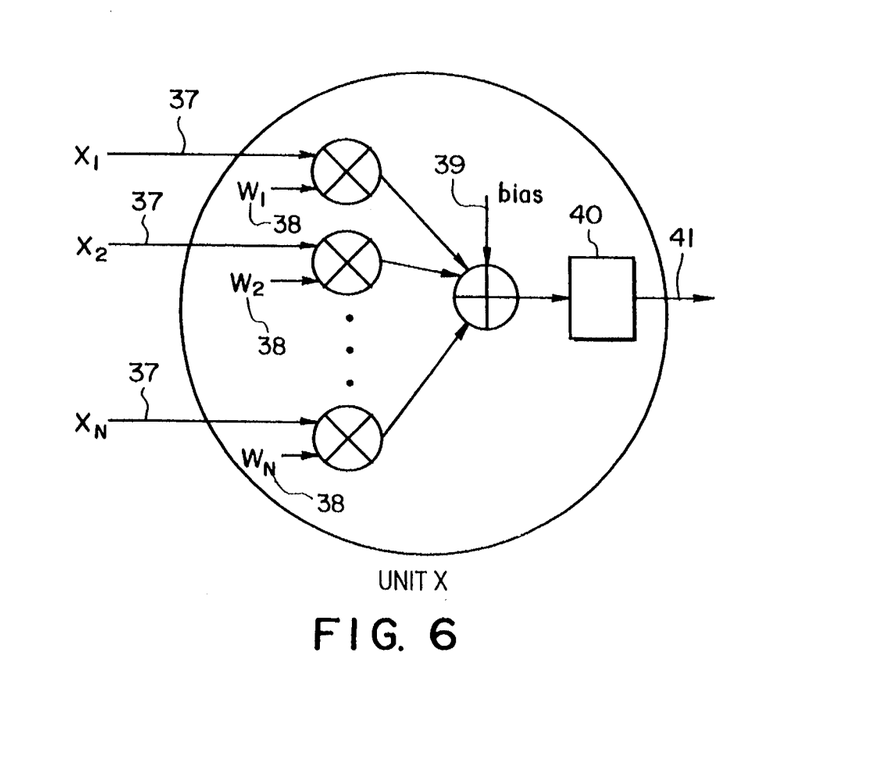
FIG. 6 is a schematic view illustrating a particular unit in the neural network according to an embodiment the present invention.

In addition, the neural network 20 comprises thirty hidden layer units 34 and one output layer unit 35. FIG. 6 is a schematic depiction of an arbitrary unit ("Unit X") corresponding to a hidden layer unit 34 or to the output layer unit 35. With unit X corresponding to a particular hidden layer unit 34, the plurality of inputs 37 ($X_1$–$X_n$) correspond to the plurality of digital words 33 from the input layer 30. Each input 37 is weighted by a weight 38 ($W_1$–$W_n$), summed with a bias term 39, and processed by a sigmoidal nonlinearity 40. An output value 41 is outputted to the output layer unit 35. With unit X corresponding to the output layer unit 35, each of the plurality of inputs 37 ($X_1$–$X_n$) corresponds to the outputted value from each of the hidden layer units 34. An output value 41, corresponding to the neural network output value 36, is outputted by the output layer unit 35. Thus, the neural network 20 is fully interconnected with a weight from each input layer unit 30 to each hidden layer unit 34, and from each hidden layer unit 34 to the output layer unit 35, and a bias term 39 for each unit. Bipolar sigmoidal nonlinearities 40 are used for all hidden layer units 34 and the output layer unit 35. In equation form, the neural network can be described as follows:

The input to each hidden layer unit 34 is of the form:

$$g_i = \sum_{j=0}^{19} W_{ij} x(j) + b_i$$

for $0 \leq i \leq 29$
where
  $g_i$=input to $i^{th}$ hidden unit
  $W_{ij}$=weight from input j to hidden unit i
  $x(j)$=$j^{th}$ input
  $b_i$=bias for hidden unit i
The output of each hidden layer unit 34 is of the form:

$$h_i = \frac{1 - e^{-g_i}}{1 + e^{-g_i}}$$

where
  $g_i$=input to $i^{th}$ hidden unit
  $h_i$=output of $i^{th}$ hidden unit
The input to the final output layer unit 35 is of the form:

$$O = \sum_{j=0}^{29} wh_j\, h_j + b$$

where
  O=input to output unit
  $wh_j$=weight from $j^{th}$ hidden unit to output unit 35
  $h_j$=output of jth hidden unit
  b=bias for output unit 35
The final output, i.e., from the output layer unit 35, is given by:

$$p = \frac{1}{1 + e^{-O}}$$

where
  p=output of output unit 35
  O=input of output unit

Figure 7:
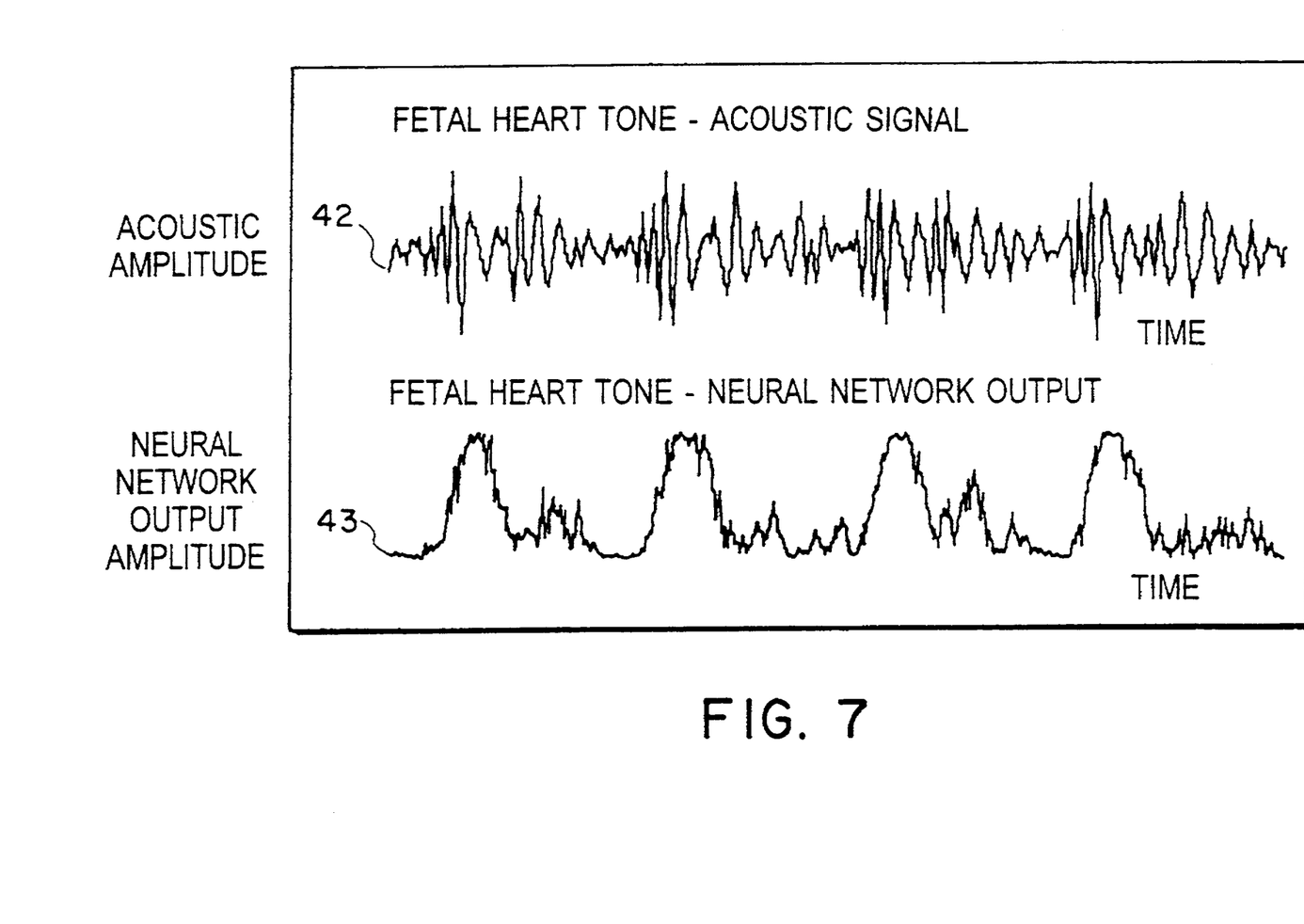
FIG. 7 is a graph showing the time domain acoustic fetal heart signal and the neural network response to the signal according to an embodiment of the present invention.

The neural network 20 was trained with a back propagation method using hand labeled training data, wherein regions of fetal heart beats and between-beat intervals were previously identified. Such data were obtained from clinical tests. Backpropagation is a well known method in the industry used to train a neural network, as described in Lippmann, R. P., "An Introduction to Computing with Neural Nets," IEEE ASSP magazine, April 1987, pp. 4–22 (hereafter "Lippman"). The values for the weights and bias terms were determined from this training procedure. After the completion of the training, the neural network 20 operates using the learned weights and biases. In essence, the neural network 20 acts as a nonlinear filter trained to indicate the presence of a fetal heart beat. FIG. 7 is a graph showing an example of a fetal heart tone as represented by an acoustic signal 42 and the resulting, nonlinearly filtered time-domain output waveform 43 from the neural network 20. The acoustic signal 42 shown in FIG. 7 is the amplitude of the acoustic signal as time passes. The neural network output waveform 43 is the amplitude of the neural network output as time passes.

As regards the neural network 20, although a layered, interconnected, feed forward neural network is caused to learn by back propagation, the embodiments of the present invention are not limited to this choice of a neural network nor to this choice of training. For example, an interlinked feed forward neural network also having feed back connections can be used. Such a feed forward and feed back neural network can be trained by a method proposed by J. J. Hopfield or another by G. E. Hinton et al. These learning methods are described in Hopfield, J. J., "Neural network and physical systems with emergent collective computational abilities," Proc. Natl. Acad. Sci. U.S.A., 1982, vol. 79; Hopfield, J. K., "Neurons with graded response have collective computational properties like those of two-state neurons," Proc. Natl. Acad. Sci. U.S.A., 1984, vol. 81; Ackley, D. H., Hinton, G. E., and Senjnowski, T. J., "A Learning Algorithm for Boltzmann Machines," Cognitive Sci., 1985, 9. Other variations of the neural network are also possible. For example, neural networks having a different number of hidden units, output units, or layers may also be trained to identify fetal heart beats.

The resulting signal from each of the multiple parallel nonlinear filtering is then analyzed with autocorrelation processing 21 (as shown in FIG. 3) as a first step in determining a fetal heart rate estimate 23. The determination of a fetal heart rate estimate for each of the plurality of results from the multiple parallel nonlinear filtering of each of the plurality of sensor signals 17 will increase the chances of discovering the most accurate fetal heart rate estimate.

Peak evaluation processing 22, as the next step as shown in FIG. 3, identifies peaks, selects the highest peaks, estimates a fetal heart rate based on the selected peaks in the autocorrelation, and determines a figure of merit 24 for the fetal heart rate estimate 23. A peak is defined as a point in the autocorrelation which is larger than immediately adjacent points. A peak is selected for fetal heart rate estimation if the peak is larger than a threshold number of adjacent points. A heart rate estimate is found by identifying and using the selected peaks in the autocorrelation over a search range appropriate for fetal heart rates (typically 80 to 200 beats per minute). The heart rate estimates 23 are determined in this manner for each of the multiple sensor channels. The heart rate estimates 23 are then ranked using a figure of merit 24, which is derived from continuity constraints and a measure of periodicity in the waveform, as described below. The highest ranking (i.e., having the highest figure of merit) estimate is then selected in the next step by the merit comparison processing 25 as the heart rate 26 for the current frame of data. The figure of merit 27 is the figure of merit value corresponding to the selected fetal heart rate 26. This procedure is repeated for each frame of data. The time between frames for the entire processing is very small (e.g., 0.5 sec.) in order to properly monitor dynamic real-time changes in fetal heart rates.

The figure of merit 24 is determined as follows. First, one buffer is used to store a small number (e.g., 5) of the previously selected values of fetal heart rate 26. Another buffer is used to store a corresponding small number (e.g., 5) of the previously corresponding values of figure of merit. A small number of previously calculated fetal heart rates and corresponding merit values is used to ensure the best dynamic response to fetal heart rate changes. A calculation is made using the following variables and equations:

For $i^{th}$ rate estimate, $$\text{Merit} = \text{Peak}(i) * \left(1.0 - \frac{\text{Avg. Merit}}{\text{Rate Dev.}}\right) * (\text{Rate}(i) - \text{Avg. Rate})$$

where
  Merit=Figure of merit for the $i^{th}$ fetal heart rate estimate.
  Peak(i)=The normalized autocorrelation for the $i^{th}$ fetal heart rate estimate.

$$\text{Avg. Merit} = \frac{1}{m+1} \sum_{i=0}^{m} \text{Merit}(i)$$

where m is a small number (e.g., 4, which will provide for five samples when i ranges from 0 to 4), and Merit(i)=previous merit computations 27

Rate Dev.=The factor which controls the contribution of previous estimates (typically=30).

Rate(i)=fetal heart rate estimate 23

$$\text{Avg. Rate} = \frac{\sum_{i=0}^{m} \text{Merit}(i) \cdot \text{Rate}(i)}{\sum_{i=0}^{m} \text{Merit}(i)}$$

where m is a small number (e.g., 4, which will provide for five samples when i ranges from 0 to 4);

Merit(i)=previous merit computations 27; and

Rate(i)=previous selected rates 26.

This Avg. Rate is the "weighted" average of a small number m of previously selected fetal heart rates 26 having the highest ranking merits 27 when these rates 26 were selected by the merit comparison operation 25.

The heart rate estimate 23 with the highest figure of merit 24 is selected as the current and most accurate fetal heart rate 26 during merit comparison 25. If the figure of merit 27 for this calculation is above an empirically determined threshold (typically about 35% of the maximum value), the resultant calculation is assumed to be valid. When and if the output heart rate 26 is determined to be valid and is to be displayed, it is displayed as a "correct" reading. If the merit 27 is lower than the empirical threshold value (i.e., an invalid rate), the rate 26 is still displayed, but is color coded in the computer display to indicate a possible error or "dropout."

Figure 8:
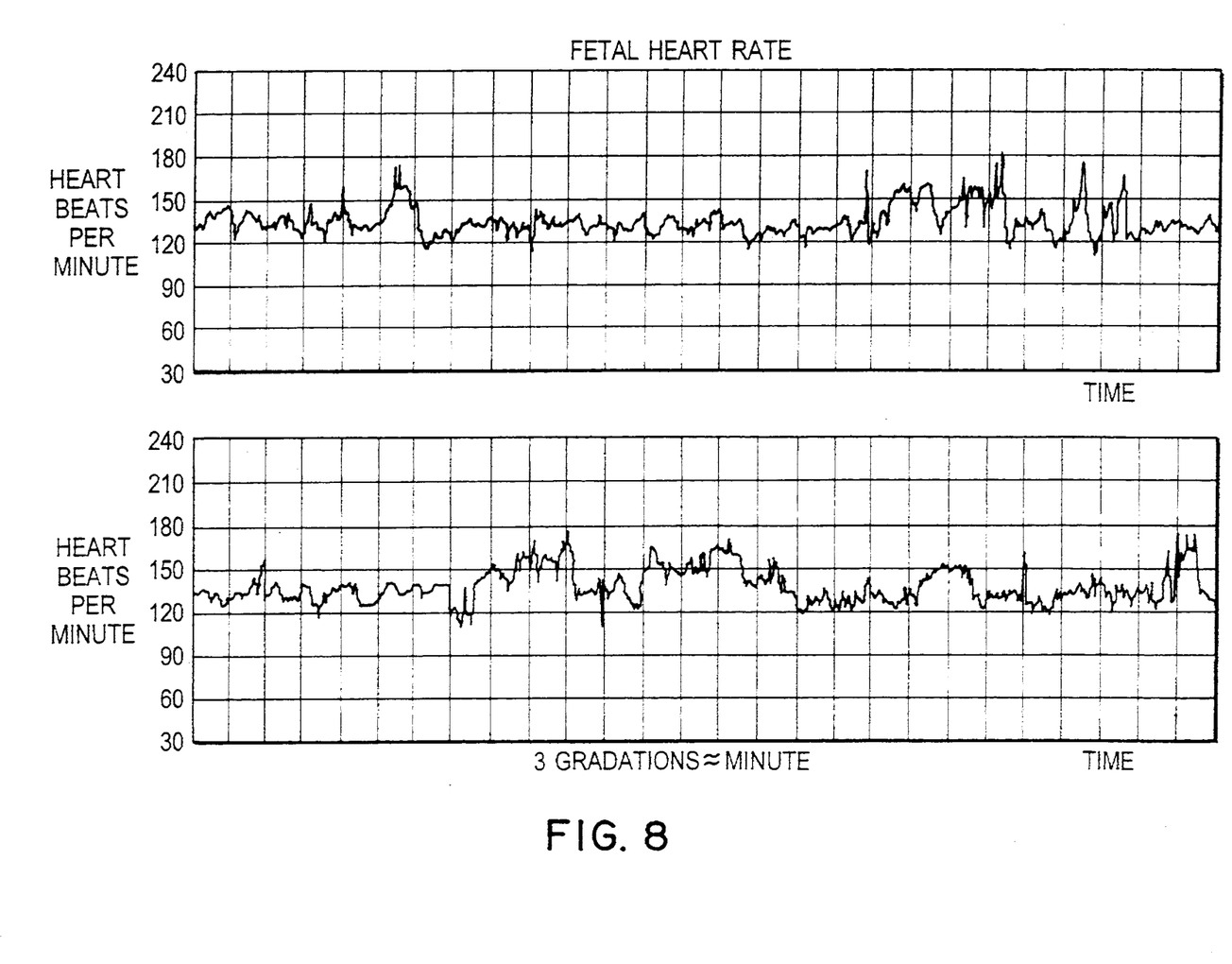
FIG. 8 is a graph depicting the fetal heart rate tracing obtained from acoustic monitoring of a patient with a gestation age of 39 weeks.

Alternatively, the outputted fetal heart rates 26 may be saved in fixed disk storage on the PC or transmitted to a communications channel, such as a modem. An example of an output tracing of fetal heart rates from a device for an embodiment according to the present invention, obtained from a patient with a gestation age of 39 weeks, is shown in FIG. 8. The y-axis is measured in beats per minute versus time as measured along the X-axis. Each gradation along the X-axis equals approximately 20 seconds, or three gradations for about a minute.

Numerous modifications and adaptations of the present invention will be apparent to those skilled in the art. Thus, the following claims and their equivalents are intended to cover all such modifications and adaptations which fall within the true spirit and scope of the present invention.

What is claimed is:

1. A passive fetal heart rate monitoring apparatus comprising:

a passive fetal heart rate monitoring sensor having a plurality of sensor elements for acquiring acoustic signals emitted from a fetus inside a body and outputting a plurality of sensor signals in response to the acoustic signals;

a signal processing device, including receivers, amplifiers, and filters for outputting a plurality of processed signals in response to the sensor signals;

means for detecting fetal heart beats comprising a neural network, responsive to the plurality of processed signals, for identifying regions of fetal heart beats on each signal, and for outputting a functional value indicative of the presence of fetal heart beats for each processed signal;

fetal heart rate determining means, responsive to the plurality of functional values indicative of the presence of fetal heart beats, for determining and outputting a fetal heart rate.

2. An apparatus as in claim 1, wherein said neural network comprises an input layer, a hidden layer, and an output layer, each layer comprising one or more nodes, a first node in the input layer being connected to the current input processed signal, and all other nodes in the input layer being connected to a different previous input point corresponding to a previous input processed signal, each node in the input layer being connected to each node in the hidden layer and each node in the hidden layer being connected to each node in the output layer, the output layer outputting a functional value indicative of fetal heart beats, each connection between nodes having an associated weight; and a training means for determining the weight for each said connection between nodes of the neural network.

3. An apparatus as in claim 2 wherein the training means comprises means for adjusting each weight by use of back propagation.

4. An apparatus as in claim 1, wherein said means for detecting fetal heart beats further comprises a plurality of neural networks connected in parallel to said neural network for providing redundant identification of the fetal heart beats from the signal, and outputting a plurality of functional values indicative of the presence of fetal heart beats for each processed signal.

5. An apparatus as in claim 1, wherein said means for detecting fetal heart beats further comprises a Teager Energy Operator connected in parallel to said neural network for providing redundant identification of the fetal heart beats for each received processed signal by outputting a plurality of functional values indicative of the presence of fetal heart beats for each processed signal, said Teager Energy Operator is defined by the equation:

$$y(n) = x^2(n-1) - x(n) \cdot x(n-2)$$

where x(n) is the processed signal and y(n) is the functional value.

6. An apparatus as in claim 1 wherein the fetal heart rate determining means comprises:

means for determining and outputting a fetal heart rate estimate for each of the received functional values;

means for ranking the estimated fetal heart rates by determining a figure of merit value for each received fetal heart rate estimate; and merit comparison processing means for comparing the received figure of merit values for each received estimated fetal heart rate and outputting the estimated fetal heart rate which has the highest figure of merit.

7. An apparatus as in claim 6, wherein said means for determining and outputting a fetal heart rate estimate comprises:

an autocorrelator for forming an autocorrelation function responsive to each of the received plurality of functional values, and means for detecting peaks for each received autocorrelation function over a search range appropriate for fetal heart rates, converting the peaks into an estimated fetal heart rate for each autocorrelation function, and outputting each of the plurality of estimated heart rates.

8. An apparatus as in claim 1 further comprising display means for receiving and displaying the estimated fetal heart rate with the highest figure of merit.

9. An apparatus as in claim 1 wherein said signal processing device further comprises an analog to digital converter for digitizing the plurality of sensor signals.

10. A passive fetal heart rate monitoring apparatus comprising:

a passive fetal heart rate monitoring sensor having a plurality of sensor elements for acquiring acoustic signals emitted from a fetus inside a body and outputting a plurality of sensor signals in response to the acoustic signals;

a signal processing device, including receivers, amplifiers, and filters for outputting a plurality of processed signals in response to the sensor signals;

means for detecting fetal heart beats comprising a Teager Energy Operator, responsive to the plurality of processed signals, for identifying regions of fetal heart beats on each signal, and for outputting a functional value indicative of the presence of fetal heart beats for each processed signal;

fetal heart rate determining means, responsive to the plurality of functional values indicative of the presence of fetal heart beats, for determining and outputting a fetal heart rate.

11. An apparatus as in claim 10 wherein said Teager Energy Operator is defined by the equation:

$$y(n) = x^{\wedge}2*(n-1) - x(n)*(n-2)$$

where x(n) is the processed signal and y(n) is the functional value.

12. An apparatus as in claim 10 wherein said means for detecting fetal heart beats further comprises Teager Energy Operators connected in parallel to said Teager Energy Operator for providing redundant identification of the fetal heart beats for each received processed signal by outputting a plurality of functional values indicative of the presence of fetal heart beats for each processed signal.

13. An apparatus as in claim 10 wherein the fetal heart rate determining means comprises:

means for determining and outputting a fetal heart rate estimate for each of the received functional values;

means for ranking the estimated fetal heart rates by determining a figure of merit value for each received fetal heart rate estimate; and merit comparison processing means for comparing the received figure of merit values for each received estimated fetal heart rate and outputting the estimated fetal heart rate which has the highest figure of merit.

14. An apparatus as in claim 13, wherein said means for determining and outputting a fetal heart rate estimate comprises:

an autocorrelator for forming an autocorrelation function responsive to each of the received plurality of functional values, and means for detecting peaks for each received autocorrelation function over a search range appropriate for fetal heart rates, converting the peaks into an estimated fetal heart rate for each autocorrelation function, and outputting each of the plurality of estimated heart rates.

15. An apparatus as in claim 10 further comprising display means for receiving and displaying the estimated fetal heart rate with the highest figure of merit.

16. An apparatus as in claim 10 wherein said signal processing device further comprises an analog to digital converter for digitizing the plurality of sensor signals.

17. A method for passive fetal heart rate monitoring of a fetus in a body comprising:

acquiring acoustic signals emitted from a fetus inside a body and outputting a plurality of sensor signals in response to the acoustic signals;

receiving, amplifying, and filtering outputting a plurality of processed signals in response to the sensor signals;

detecting fetal heart beats using a neural network, responsive to the plurality of processed signals, identifying regions of fetal heart beats on each signal, and outputting a functional value indicative of the presence of fetal heart beats for each processed signal;

determining and outputting the fetal heart rate in response to the plurality of functional values indicative of the presence of fetal heart beats.

18. The method of claim 17, wherein said neural network comprises an input layer, a hidden layer, and an output layer, each layer comprising one or more nodes, a first node in the input layer being connected to the current input processed signal, and all other nodes in the input layer being connected to a different previous input point corresponding to a previous input processed signal, each node in the input layer being connected to each node in the hidden layer and each node in the hidden layer being connected to each node in the output layer, the output layer outputting a functional value indicative of fetal heart beats, each connection between nodes having an associated weight; and a training means for determining the weight for each said connection between nodes of the neural network.

19. The method of claim 18 wherein the training means comprises means for adjusting each weight by use of back propagation.

20. The method of claim 17, wherein the step of detecting fetal heart beats further comprises the steps of providing redundant identification of the fetal heart beats from each signal using a plurality of neural networks connected in parallel to said neural network and responsive to each signal, and outputting a plurality of functional values indicative of the presence of fetal heart beats for each processed signal.

21. The method of claim 17, wherein the step of detecting fetal heart beats further comprises the steps of providing redundant identification of the fetal heart beats for each received processed signal using a Teager Energy Operator connected in parallel to said neural network and responsive to each signal, and outputting a plurality of functional values indicative of the presence of fetal heart beats for each processed signal, said Teager Energy Operator is defined by the equation:

$$y(n) = x^{\wedge}2*(n-1) - x(n)*(n-2)$$

where x(n) is the processed signal and y(n) is the functional value.

22. The method of claim 17 wherein the fetal heart rate determining means comprises:

determining and outputting a fetal heart rate estimate for each of the received functional values;

ranking the estimated fetal heart rates by determining a figure of merit value for each received fetal heart rate estimate; and comparing the received figure of merit values for each received estimated fetal heart rate and outputting the estimated fetal heart rate which has the highest figure of merit.

23. The method of claim 22, wherein the step of determining and outputting a fetal heart rate estimate comprises:

forming an autocorrelation function responsive to each of the received plurality of functional values, detecting peaks for each received autocorrelation function over a search range appropriate for fetal heart rates, converting the peaks into an estimated fetal heart rate for each autocorrelation function, and outputting each of the plurality of estimated heart rates.

24. The method of claim 17 further comprising the steps of receiving and displaying the estimated fetal heart rate with the highest figure of merit.

25. The method of claim 17 wherein the step of processing the signals further comprises the step of digitizing the plurality of sensor signals.

26. A passive fetal heart rate monitoring method comprising the steps of:

acquiring acoustic signals emitted from a fetus inside a body and outputting a plurality of sensor signals in response to the acoustic signals;

processing the signals using a signal processing device having receivers, amplifiers, and filters, and outputting a plurality of processed signals in response to the sensor signals;

detecting fetal heart beats using a Teager Energy Operator responsive to the plurality of processed signals, identifying regions of fetal heart beats on each signal, and outputting a functional value indicative of the presence of fetal heart beats for each processed signal;

determining and outputting a fetal heart rate in response to the plurality of functional values indicative of the presence of fetal heart beats.

27. The method of claim 26 wherein said Teager Energy Operator is defined by the equation:

$$y(n) = x^2(n-1) - x(n)*x(n-2)$$

where $x(n)$ is the processed signal and $y(n)$ is the functional value.

28. The method of claim 26 wherein the step of detecting fetal heart beats further comprises the steps of providing redundant identification of the fetal heart beats for each received processed signal by connecting a plurality of Teager Energy Operators in parallel to said Teager Energy Operator and outputting a plurality of functional values indicative of the presence of fetal heart beats for each processed signal.

29. The method of claim 26 wherein the fetal heart rate determining means comprises:

determining and outputting a fetal heart rate estimate for each of the received functional values;

ranking the estimated fetal heart rates by determining a figure of merit value for each received fetal heart rate estimate; and comparing the received figure of merit values for each received estimated fetal heart rate and outputting the estimated fetal heart rate which has the highest figure of merit.

30. The method of claim 29, wherein the step of determining and outputting a fetal heart rate estimate comprises:

forming an autocorrelation function responsive to each of the received plurality of functional values, detecting peaks for each received autocorrelation function over a search range appropriate for fetal heart rates, converting the peaks into an estimated fetal heart rate for each autocorrelation function, and outputting each of the plurality of estimated heart rates.

31. The method of claim 26 further comprising the steps of receiving and displaying the estimated fetal heart rate with the highest figure of merit.

32. The method of claim 26 wherein the step of processing the signals further comprises the step of digitizing the plurality of sensor signals.

* * * * *